US011684422B2

(12) United States Patent
Warner et al.

(10) Patent No.: US 11,684,422 B2
(45) Date of Patent: Jun. 27, 2023

(54) SYSTEM AND METHOD FOR OPTIMAL CATHETER SELECTION FOR INDIVIDUAL PATIENT ANATOMY

(71) Applicant: General Electric Company, Schenectady, NY (US)

(72) Inventors: Adrian F. Warner, Wauwatosa, WI (US); James V. Miller, Niskayuna, NY (US); Daniel R. Schneidewend, Wauwatosa, WI (US); Hao Lai, Niskayuna, NY (US); Maxime Cazalas, Buc (FR); Hans-Peter Stoll, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 437 days.

(21) Appl. No.: 16/517,973

(22) Filed: Jul. 22, 2019

(65) Prior Publication Data

US 2019/0336224 A1 Nov. 7, 2019

Related U.S. Application Data

(62) Division of application No. 14/858,770, filed on Sep. 18, 2015, now Pat. No. 10,398,509.

(51) Int. Cl.
*A61B 34/10* (2016.01)
*G16H 50/50* (2018.01)
(Continued)

(52) U.S. Cl.
CPC ............ *A61B 34/10* (2016.02); *A61B 5/0044* (2013.01); *A61B 5/055* (2013.01); *A61B 6/032* (2013.01);
(Continued)

(58) Field of Classification Search
CPC ....... A61B 34/10; A61B 5/0044; A61B 5/055; A61B 6/032; A61B 6/12; A61B 6/5211;
(Continued)

(56) References Cited

U.S. PATENT DOCUMENTS 5,054,496 A    10/1991  Wen et al.
5,687,737 A    11/1997  Branham et al.
(Continued)

FOREIGN PATENT DOCUMENTS

EP        0339799         10/1994
WO     2010025336 A1      3/2010

OTHER PUBLICATIONS

Ikari et al., "Initial Characterization of Ikari Guide Catheter for Transradial Coronary Intervention", Journal of Invasive Cardiology, vol. 16, Issue 2, Feb. 2004.
(Continued)

*Primary Examiner* — Bo Joseph Peng
(74) *Attorney, Agent, or Firm* — Boyle Fredrickson, S.C.

(57) ABSTRACT

In the present invention, a system and method for selection of an optimal catheter for use in a medical procedure relative to the anatomy of a patient includes the steps of providing a system including a scanning device capable of obtaining image data on a ROI within the anatomy of a patient and reconstructing a 3D image of the ROI from the image data, a display capable of illustrating the 3D image and a 3D catheter model, and a CPU operably connected to the scanning device and the display and operable to analyze the 3D image in comparison with the 3D catheter model, obtaining image data of the ROI of the patient, reconstructing a 3D image of the ROI from the image data and comparing the 3D catheter model with the 3D image of the ROI to determine the catheter with the optimal configuration for use in the procedure.

3 Claims, 4 Drawing Sheets

(51) Int. Cl.
  *G06T 7/11* (2017.01)
  *A61B 6/12* (2006.01)
  *A61B 5/00* (2006.01)
  *A61B 5/055* (2006.01)
  *A61B 6/03* (2006.01)
  *A61B 6/00* (2006.01)
  *G06T 11/00* (2006.01)
  *G06T 17/00* (2006.01)

(52) U.S. Cl.
  CPC .............. *A61B 6/12* (2013.01); *A61B 6/5211* (2013.01); *G06T 7/11* (2017.01); *G06T 11/003* (2013.01); *G06T 17/00* (2013.01); *G16H 50/50* (2018.01); *A61B 6/4441* (2013.01); *A61B 6/466* (2013.01); *A61B 6/487* (2013.01); *A61B 6/503* (2013.01); *A61B 6/504* (2013.01); *A61B 2034/108* (2016.02); *A61B 2576/023* (2013.01); *G06T 2207/10072* (2013.01); *G06T 2207/20112* (2013.01); *G06T 2207/30021* (2013.01); *G06T 2207/30048* (2013.01); *G06T 2207/30101* (2013.01)

(58) Field of Classification Search
  CPC ....... A61B 6/4441; A61B 6/466; A61B 6/487; A61B 6/503; A61B 6/504; A61B 2034/108; A61B 2576/023; A61B 6/461; A61B 6/469; G06T 7/11; G06T 11/003; G06T 17/00; G06T 2207/10072; G06T 2207/20112; G06T 2207/30021; G06T 2207/30048; G06T 2207/30101; G16H 50/50
  See application file for complete search history.

(56) References Cited

U.S. PATENT DOCUMENTS

| | | |
|---|---|---|
| 5,798,761 A | 8/1998 | Isaacs |
| 5,957,911 A | 9/1999 | Nesto |
| 6,603,996 B1 | 8/2003 | Beatty et al. |
| 7,996,063 B2 | 8/2011 | Vass et al. |
| 8,184,886 B2 | 5/2012 | Khamene et al. |
| 8,274,506 B1 | 9/2012 | Rees |
| 8,472,746 B2 | 6/2013 | Wei et al. |
| 8,649,479 B2 | 2/2014 | De Man et al. |
| 8,948,853 B2 | 2/2015 | Harley et al. |
| 2002/0137014 A1 | 9/2002 | Anderson et al. |
| 2004/0077942 A1 | 4/2004 | Hall et al. |
| 2008/0033293 A1 | 2/2008 | Beasley |
| 2008/0221438 A1* | 9/2008 | Chen ...................... A61B 5/287 600/424 |
| 2009/0012533 A1 | 1/2009 | Barbagli et al. |
| 2010/0097374 A1 | 4/2010 | Fan et al. |
| 2010/0152828 A1 | 6/2010 | Pakbaz et al. |
| 2010/0185172 A1 | 7/2010 | Fabro |
| 2010/0239148 A1 | 9/2010 | Zheng et al. |
| 2012/0232853 A1 | 9/2012 | Voigt et al. |
| 2013/0184569 A1 | 7/2013 | Strommer et al. |
| 2014/0071130 A1 | 3/2014 | Piemonte |
| 2014/0094814 A1 | 4/2014 | Hughes et al. |
| 2014/0107453 A1 | 4/2014 | Maskara et al. |
| 2014/0187989 A1 | 7/2014 | Thakura et al. |
| 2014/0200457 A1 | 7/2014 | Shuros et al. |
| 2014/0235988 A1 | 8/2014 | gosh |
| 2015/0119671 A1 | 4/2015 | Varma |

OTHER PUBLICATIONS

Giubilato et al., "Percutaneous, Recanalization of Chronic Total Occlusion (CTO) Coronary Arteries: Looking Back AnD Moving Forward", InTech, Chapter 20, 2013, 42 pages.

* cited by examiner

SYSTEM AND METHOD FOR OPTIMAL CATHETER SELECTION FOR INDIVIDUAL PATIENT ANATOMY

This application is a divisional of U.S. application Ser. No. 14/858,770, filed Sep. 18, 2015, the entirety of which is incorporated herein.

BACKGROUND OF INVENTION

The invention relates generally to identification systems for catheters, arid more particularly to identification systems that enable the most effective or optimal catheter for use in a procedure to be selected prior to utilizing the catheter in the actual procedure.

Catheters are used in an increasing number of medical procedures to evaluate various conditions of the patient with which the catheter is utilized. These catheters are inserted into the patient and positioned at the desired location where the catheter can be utilized to treat the patient in the prescribed manner.

While many different numbers and/or configurations of catheters can potentially be utilized for a particular procedure, such as an interventional cardiac procedure, the anatomy of the individual patient on which the procedure is to be performed often differs from patient to patient. As such, a catheter that may perform well when performing the procedure on one patient may not be useful when performing the same or a similar procedure on a different patient. Thus, when one catheter is found not to work in a procedure as a result of difference in the anatomy of the particular patient, the clinician has to remove the initial catheter used and insert a second, differently shaped catheter to attempt to accommodate the anatomy of the particular patient to perform the procedure.

This process can be repeated multiple times in order to arrive at a catheter having a shape complementary to the patient anatomy in order to perform the procedure. As such, selecting the appropriate catheter shape and size for various procedures, such as cardiac catheterization procedures, relative to the patient's anatomy is challenging, and potentially wasteful in catheters, as well as physician time. Further, the repeated catheter insertions and removals to achieve the proper catheter configuration for the patient's anatomy can increase the chances of a. potential for injury in the ascending aorta and the coronary orifices;
  b. potential for "liberating" plaque material from the arterial wall with subsequent embolization into brain or periphery;
  c. potential for mechanical injury at the arterial access site; or
  d. overall adverse event rate of the procedure.

In order to mitigate these issues, certain prior art attempts have been made to reduce the need for insertion of multiple catheters to accommodate the anatomy of a particular patient. For example, in U.S. Pat. No. 7,996.063 and U.S. Patent Application Publication No. US2004/0077942, a three-dimensional (3D) image of the patient anatomy is reconstructed from scans taken of the area of interest. This 3D image is then utilized with a catheter that can be viewed in conjunction with the 3D image on the display in order to guide the catheter along the desired path through the tissue represented in the 3D image during the procedure.

However, even with the ability to use the 3D image to guide the catheter through the tissue shown in the image, due to differences in the structure of the anatomy of a patient, on many occasions it is still necessary to remove a catheter of a particular type for substitution by a catheter with another configuration in order to successfully navigate the desired path through the patient.

Accordingly, it is desirable to develop an identification system and method for identifying an optimal catheter configuration that can successfully navigate the desired pathway through the individual patient anatomy prior to insertion of the catheter into the patient.

BRIEF DESCRIPTION OF THE INVENTION

There is a need or desire for a system and method to identify a catheter with an optimal configuration capable of navigating a pathway through an individual patient's anatomy to an area of interest located within a 3D image of tissue to be treated within the patient. The above-mentioned drawbacks and needs are addressed by the embodiments described herein in the following description.

According to one exemplary aspect of the invention, an optimal catheter selection system and method includes an imaging device, which can be a pre-procedure magnetic resonance imaging (MRI) device or x-ray computed tomography (CT) device, as well as optionally an in-procedure 3D angio-rotation scanning device, that is capable of scanning a patient and obtaining data from the scans that can be utilized to reconstruct a 3D image of the scanned portion(s) of the patient that is viewable on a display connected to the scanning device. The 3D image, and in particular the specific area of interest in the 3D image relevant to the procedure to be performed, is then analyzed in comparison with the configurations of multiple catheters in order to determine which catheter has an optimal configuration most compatible with the structure of the area of interest. The system and method permits visualization of the various catheter configurations relative to a specific 3D image of the patient anatomy to help ensure successful and optimal selection of the catheter to be utilized in various procedures, such as cardiac procedures.

According to another aspect of an exemplary embodiment off the invention, the method of analysis of the catheter configurations with the 3D model of the patient anatomy is performed automatically by a central processing unit of the system, manually by the clinician, or using a combination of these methods. The system includes a library of 3D models of standard catheter sizes, shapes and types that can directly be compared with the 3D model of the patients individual anatomy for selection of the optimal catheter configuration to be utilized.

According to still another aspect of one exemplary embodiment of the invention, a catheter selection system for determining a catheter having an optimized configuration for use in a medical procedure includes a scanning device capable of obtaining image data on a region of interest (ROD within the anatomy of a patient and reconstructing a three-dimensional (3D) image of the ROT from the image data, a display capable of illustrating the 3D ROT image and a 3D catheter model and a central processing unit (CPU) operably connected to the scanning device and the display, the CPU operable to analyze the 3D ROI image in comparison with the 3D catheter model.

According to still a further aspect of one exemplary embodiment of the invention, a method for selection of a catheter for use in a medical procedure having an optimal configuration relative to the anatomy of a patient on which the procedure is to be performed includes the steps of providing a system including a scanning device capable of obtaining image data on a region of interest (ROI) within the anatomy of a patient and reconstructing a three-dimensional (3D) image of the ROI from the image data; a display capable of illustrating the 3D image and a 3D catheter model; and a central processing unit (CPU) operably connected to the scanning device and the display, the CPU operable to analyze the 3D image in comparison with the 3D catheter model, obtaining image data of the ROI of the patient, reconstructing a 3D image of the ROI from the image data and comparing the 3D catheter model with the 3D image of the ROI to determine the catheter with the optimal configuration for use within the ROI to perform the procedure.

According to still a further aspect of one exemplary embodiment of the invention, a method a method for the selection of a catheter for use in a cardiac catheterization procedure having an optimal configuration relative to a heart of a patient on which the procedure is to be performed includes the steps of providing a system including a scanning device capable of obtaining image data on the heart of a patient and reconstructing a three-dimensional (3D) image of the heart from the image data; a display capable of illustrating the 3D image and a 3D catheter model; and a central processing unit (CPU) operably connected to the scanning device and the display, the CPU operable to analyze the 3D image in comparison with the 3D catheter model, obtaining image data of the heart of the patient, reconstructing a 3D image of the heart from the image data, segmenting various cardiac structures of the 3D image through which the catheter will travel and/or abut when inserted into the heart in the procedure, estimating a central axis of one or more segmented cardiac structures in the 3D image, identifying catheter support surfaces in the segmented structures of the 3D image and evaluating the fit of the 3D model within the 3D image relative to the segmented cardiac structures in the 3D image.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings

DETAILED DESCRIPTION OF THE DRAWINGS

Figure 1:
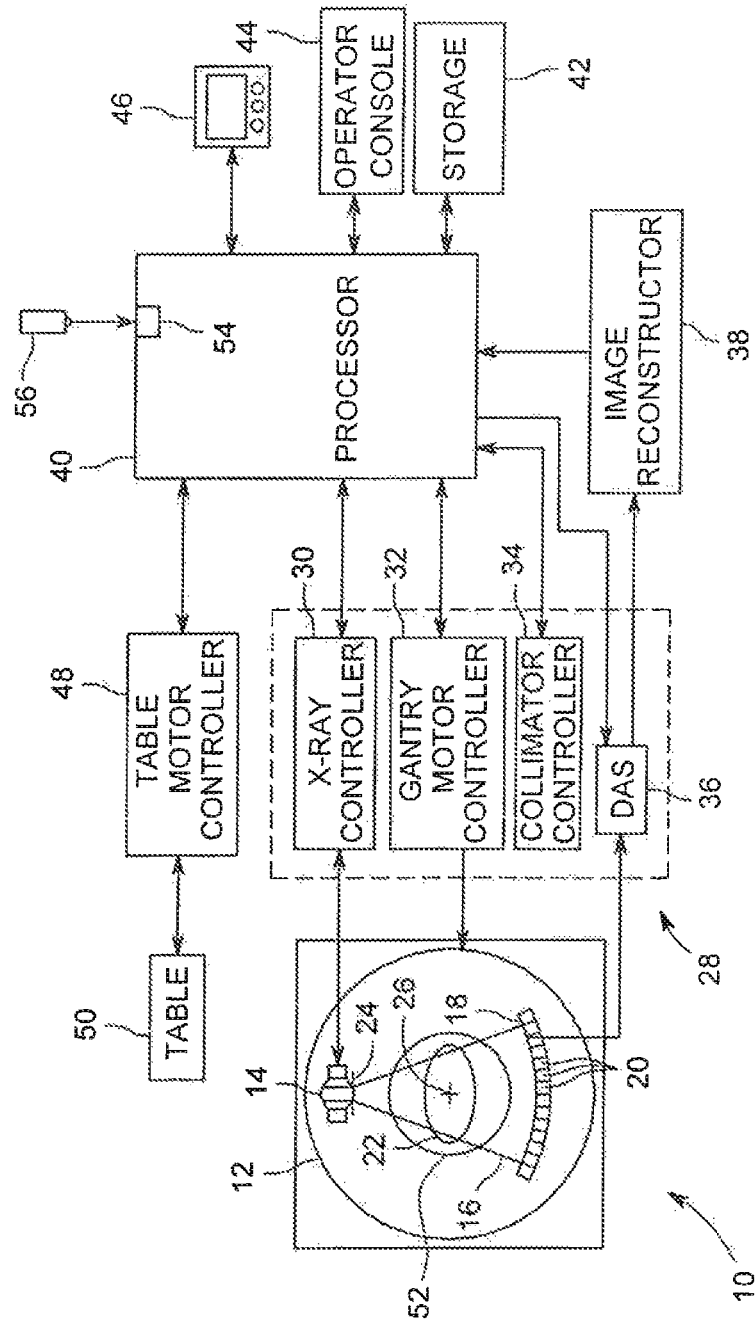
FIG. 1 is a block diagram illustrating an x-ray computed tomography (CT) imaging system for providing an image of a cardiac structure according to one exemplary embodiment of the present invention.

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to he understood that other embodiments may be utilized and that logical, mechanical, electrical and other changes may be made without departing from the scope of the embodiments. The following detailed description is, therefore, not to be taken in a limiting sense.

Further, the foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks e.g., processors, controllers or memories) may be implemented in a single piece of hardware (e.g., a general purpose signal processor or random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings.

Various embodiments provide a system 10 and associated method for obtaining data from scans of the patient to create 3D images of the areas or regions of interest of the anatomy of the patient. These can be selected from any suitable imaging device, such as a pre-procedure magnetic resonance imaging (MRI) device or x-ray computed tomography (CT) device, as well as optionally an in-procedure 3D angio-rotation scanning device, among others. In one exemplary embodiment, the system 10 is an x-ray computed tomography (CT) imaging. The CT imaging is performed in any suitable manner, such as by using dynamic region of interest (ROI) collimation control with varying x-ray beam intensity, that optionally can be utilized with a suitable contrast-enhancing agent.

FIG. 1 illustrates a simplified block diagram of an x-ray CT system 10 operable to perform imaging in accordance with one exemplary embodiment of the invention, such as that disclosed in co-owned U.S. Pat. No. 8,649,479, the entirety of which is expressly incorporated by reference herein for all purposes. The x-ray CT system 10 may be configured as a multi-slice scanning imaging system that includes a gantry 12, which may be representative of a third generation CT imaging system as described in more detail herein. The gantry 12 generally includes (e.g., supports thereon) an x-ray source 14 (also referred to as an x-ray tube) that projects an x-ray beam 16 towards a detector array 18 on the opposite side of the gantry 12. The detector array 18 is formed by a plurality of detector rows (not shown) including a plurality of detector elements 20 that together sense the projected x-rays that pass through an object, such as a patient 22 (e.g., a patient having coronary scanning performed) positioned in a supine position between the detector array 18 and the x-ray source 14.

A collimator 24 is provided in combination with the x-ray source 14 to collimate and focus the x-ray beam 16. In various embodiments, the intensity level and the collimation of the generated x-ray beam 16 are dynamically controlled and adjusted. For example, as described in more detail herein, dynamic ROI collimation and sensitive organ power modulation are provided in accordance with various embodiments.

With respect to the detector array 18, each detector element 20 produces an electrical signal that represents the intensity of an impinging x-ray beam and hence can be used to estimate the attenuation of the beam as the beam passes through the patient 22. During a scan to acquire x-ray projection data, the gantry 12 and the components mounted therein rotate about a center of rotation 26. it should be noted that although only a single row of detector elements 20 (i.e., a detector row) is shown, the detector array 18 in various embodiments is a multi-slice detector array having a plurality of parallel detector rows of detector elements 20, such that projection data corresponding to a plurality of quasi-parallel or parallel slices can be acquired simultaneously during a scan.

Rotation of the components on the gantry 12 and operation of the x-ray source 14 and collimator 24 are governed by a master controller/control mechanism 28 of the CT system 10. The control mechanism 28 includes an x-ray controller 30 that provides power and timing signals to the x-ray source 14, a gantry motor controller 32 that controls the rotational speed and position of components on the gantry 12, and a collimator controller 34 that controls collimation of the x-ray source 14 to adjust and define an ROI. For example, a field of view (FOV) of the collimator 24 is adjusted using dynamic collimation.

A data acquisition system (DAS) 36 in the control mechanism 28 samples analog data from the detector elements 20 and converts the data to digital signals for subsequent processing. An image reconstructor 38 receives sampled and digitized x-ray data from the DAS 36 and performs image reconstruction. The reconstructed image is communicated to a processor 40 (e.g., a computer), which stores the image in a storage device 42. The image reconstructor 38 can be specialized hardware or computer programs executing on the processor 40, for example, as a module.

The processor 40 also receives commands and scanning parameters from an operator via an operator console 44 that includes input devices, such as a keyboard, mouse, etc. An associated display 46 is provided, which may be any suitable display type that allows the operator to view the reconstructed image(s) and other data from the processor 40. The operator supplied commands and parameters may be used by the processor 40 to provide control signals and information to the DAS 36, x-ray controller 30, gantry motor controller 32 and collimator controller 34 as described in more detail herein. In addition, the processor 40 operates a table motor controller 48, which controls a motorized patient table 50 to position the patient 22 in the gantry 12. Particularly, the table 50 moves portions of the patient 22 through a gantry opening 52. It should be noted that the patient 22 (or a portion of the patient 22) may be moved into the gantry 12 and during imaging remain stationary during rotation of the gantry 12 or may move the patient 22 through the opening 52 during as the gantry 12 rotates.

in various embodiments, the processor 40 includes a device 54, for example, a CD-ROM drive, a DVD drive, a magnetic optical disk (MOD) device, a USB port, or any other digital device including a network connecting device such as an Ethernet device for reading instructions and/or data from a computer-readable medium 56, such as a floppy disk, a CD-ROM, a DVD, a flash memory drive (illustrated in FIG. 1) or another digital source such as a network or the Internet, as well as yet to be developed digital means. In other embodiments, the processor 40 executes instructions stored in firmware (not shown). The processor 40 is programmed to perform functions described herein, and as used herein, the term processor is not limited to just those integrated circuits referred to in the art as computers, but broadly refers to computers, microcontrollers, microcomputers, programmable logic controllers, application specific integrated circuits, and other programmable circuits, and these terms are used interchangeably herein.

Although the above-described embodiment refers to a third generation CT system, the methods described herein equally apply to fourth generation CT systems (stationary detector-rotating x-ray source) and fifth generation CT systems (stationary detector and x-ray source). Additionally, it is contemplated that the benefits of the various embodiments accrue to imaging modalities other than CT. Further, although the herein described methods and apparatus are described in a particular medical setting, it is also contemplated that the benefits of the various embodiments accrue to other applications or settings.

In operation, referring now to FIG. 2, in one exemplary embodiment of the method of the invention, the CT system 10 is operated in the following steps for determining the optimal shape or configuration for a catheter to be used in a cardiac catheterization procedure:

a. initially a pre-procedure MRI, or CT scan using the system 10, optionally with the use of a suitable contrast-enhancing agent, or an in-procedure using 3D angio-rotation scan is obtained for the heart 1000 of the patient in block 100.

b. A full scale 3D wire model/image of the heart (FIGS. 4 and 5) is reconstructed in block 102 from the scan, with the various structures of the 3D model/image being segmented to illustrated the portions of the heart 1000 through which the catheter will travel and/or abut when inserted in the procedure, which in the exemplary embodiment of the method include the ascending aorta 1002, the aortic arch 1004, the proximal descending aorta 1006 and the coronary ostiums 1008;

c. The central axis of each coronary ostium 1008 is estimated in block 104, which can be done simultaneously with or sequential to block 106, or completely as an alternative to block 106;

d. Regions of the ascending aorta 1002 and descending aorta 1006 are identified that are viable for providing a support surface 1010 to the catheter 200 when inserted in block 106, which can be done simultaneously with or sequential to block 104 or completely as an alternative to block 104;

e. In block 110 various 3D wire models of each available type of catheter 200 that are stored in an image library/database 108 connected to the system 10 are overlaid onto or otherwise evaluated in comparison with the 3D model/image of the heart 1000, such as on the display 46, to determine that the primary curve 204 of the selected catheter 200 can align the catheter tip 202 with the coronary ostium 1008, the secondary curve 206 of the catheter 200 contacts a viable support surface 1010 in the ascending aorta 1002 and that the body 208 of the catheter 200 contacts a viable support surface 1010 in the descending aorta 1006;

f. Based upon this analysis, in block 112 the catheter 200 having the best fit within the anatomy illustrated in the 3D model/image of the heart 1000 is selected for use in the procedure.

With regard to the step in block 102 of segmenting the various structure of the heart in the 3D model/image 1000, this can be accomplished in any suitable manner, including but not limited to region growing, the utilization of level sets, different model-based methods, atlas-based methods or classification approaches, as are known.

Concerning the estimation of the central axis of the ostiums 1006 in the 3D model 1000 in block 104, this can be accomplished using image moments or various model-fitting methods, as are known in the art.

For block 106, the step of locating viable catheter support surfaces 1008 can be performed utilizing various atlas-based methods, or by machine learning or similar predictive modeling procedures, where the system 10 provides the analysis based on parameters supplied to the system 10 as well as data from prior analyses stored in the system 10.

For the step in block 110 of evaluating the fit of a particular catheter 200 within the 3D image 1000, this step can be performed manually by the clinician, by the system 10, or by a combination thereof. In one exemplary embodiment, the clinician can pull the catheter models 200 of various types from the library/database 108 and for illustration on the display 46 in conjunction with the 3D image 1000. The clinician can then visually determine the catheter 200 that is the best fit for the patient anatomy illustrated in the 3D image 1000. The clinician may also highlight the 3D image 1000 at critical turning points with a drawing tool 44 when utilizing an auto-select function of the system 10. in this function, using the highlighted points in the 3D image 1000, the system 10 can analyze the catheter models 200 stored in library 108 and propose optimal catheter configurations, i.e., shapes and sizes, from the library 108. In selecting the proposed catheters 200, the system 10 can employ catheter pose estimations utilizing energy minimization, various best-fit metrics and/or machine learning predictive modeling procedures, among other suitable analysis methods. These proposed catheter models 200 can then be selected by the clinician and checked against the 3D image 1000 to ultimately determine the best or optimal catheter 200 for the procedure.

Figure 3:
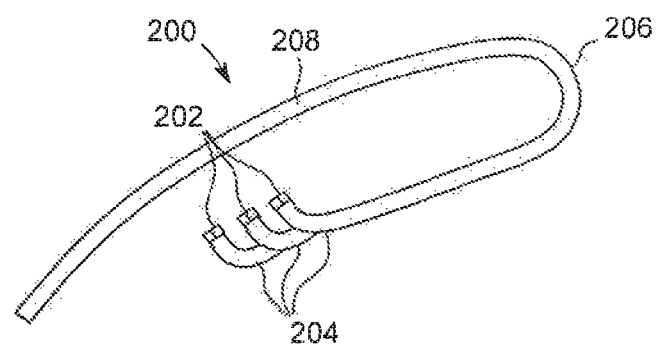
FIG. 3 is a schematic representation of examples of various catheter configurations to be analyzed in conjunction with the imaged cardiac structure according to another exemplary embodiment of the invention.
Figure 4:
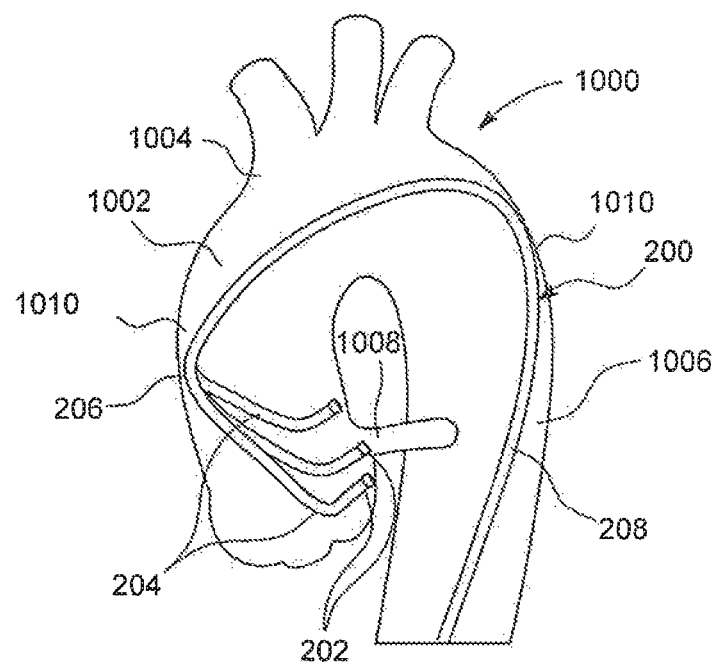
FIG. 4 is a schematic representation of the analysis of various catheter configurations within the imaged cardiac structure according to another exemplary embodiment of the invention.
Figure 5:
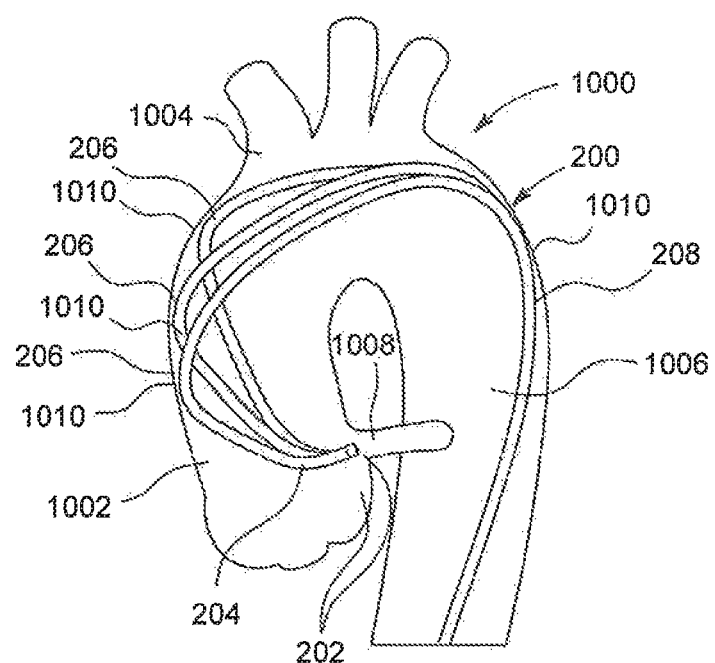
FIG. 5 is a schematic representation of the analysis of various orientations concerning the catheter support surfaces within the imaged cardiac structure according to another exemplary embodiment of the invention.

Looking at FIGS. 3-5, in an exemplary illustration of the operation of the system 10 and method, a number of 3D models of catheters 200 of varying configurations are shown in FIG. 3. These catheter models 200 are stored in the library/database 108 for retrieval and comparison/integration with the 3D image 1000 of the heart or other tissue into which the catheter 200 is to be positioned during the particular procedure. One example of how these models 200 can be obtained and/or utilized is disclosed in co-owned and co-pending U.S. patent application Ser. No. 14/328,089, filed Jul. 10, 2014, and entitled "Methods and Systems to Translate Two Dimensional Mapping into a Three Dimensional Derived Model", the entirety of which is expressly incorporated by reference herein for all purposes. In FIG. 3, as an example 3D models of a Judkins Left catheter 200 are shown with each model illustrating the catheter 200 with a different tip length.

Figure 2:
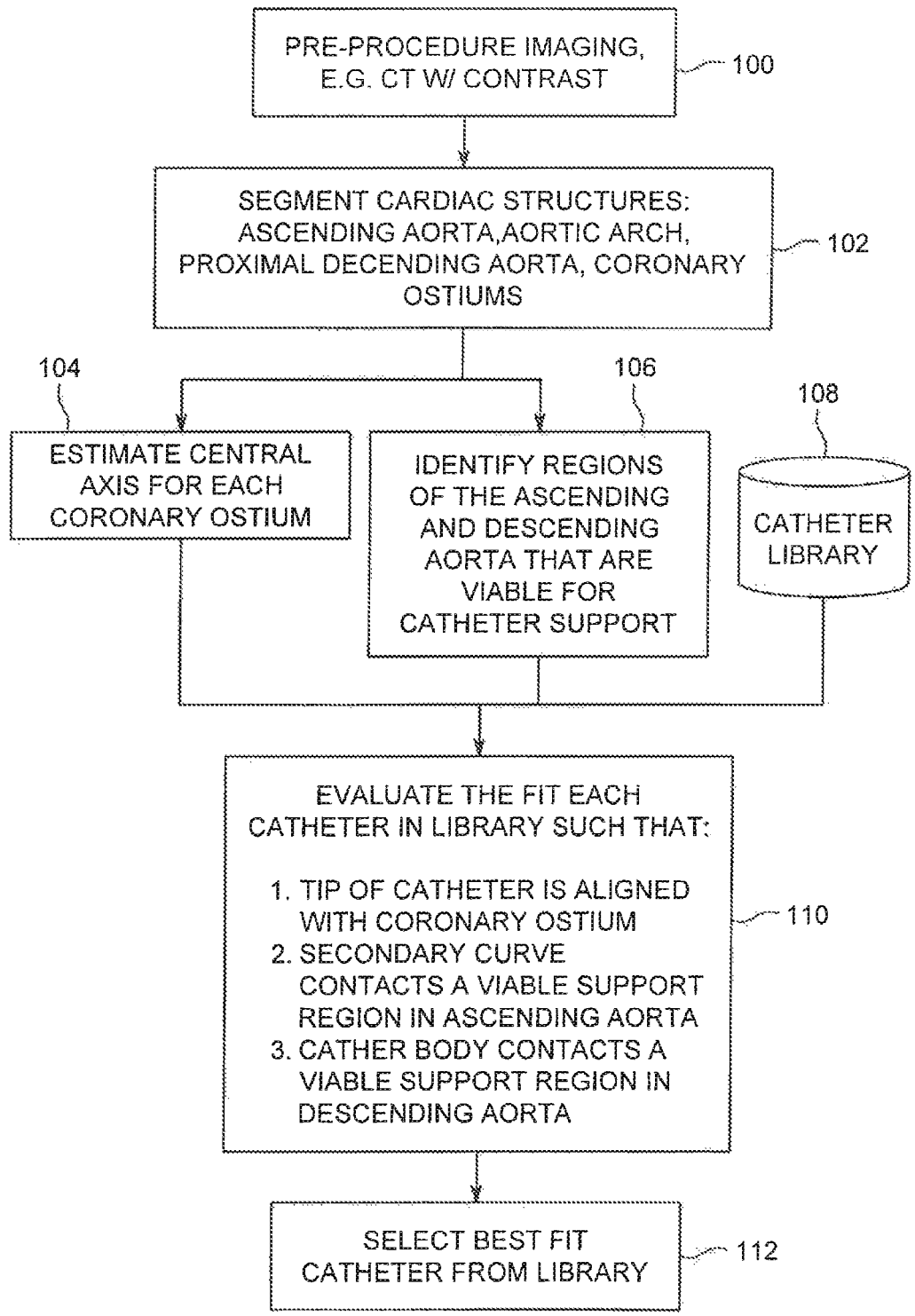
FIG. 2 is a schematic representation of a flowchart of the method of the analysis of various catheter configurations in conjunction with the imaged cardiac structure according to an exemplary embodiment of the invention.

In the analysis step in block 110 of FIG. 2, these models 200 are compared with and/or overlaid on the 3D image 1000 on the display 44 to illustrate the virtual or simulated positioning or geometrical fit of the catheters 200 within the volume of the 3D image 1000. With this positioning, it is possible to evaluate the orientation of the catheter tip 202 within the model 1000 relative to an ostium 1008 (FIG. 4) and to determine the support surfaces 1010 in the model 1000 (FIG. 5) for each of the selected catheter models 200. With this comparison/evaluation it is possible to determine of the catheter 200 having the best fit for accessing or traversing the patient's specific anatomy thereby saving time and clinical waste by avoiding the insertion of a catheter 200 having the wrong configuration. This analysis in block 110 can also be extended to include the material(s) utilized to form all or portions of the catheters 200 and/or the treatment portions thereof, e.g., the stent, balloon, or other treatment portion (not shown) to determine the catheter 200 having the optimal shape/configuration and material for use in the procedure to be conducted.

In addition to these advantages, the system 10 and method can also provide the following technical and commercial advantages:

a. The library/database of catheter models 200 can be linked to hospital inventory such that only available catheters are displayed;

b. For diagnostic angiograms there is better image quality due to a reduced amount of "lost contrast" caused by only marginally fitting coronary catheters c. For interventional procedures here is better guiding catheter "backup" through optimally fitting shape. This is a significant advantage providing better safety during the intervention through the availability of an optimally stable "access channel" to coronary lesion.

d. Shorter procedure time e. Less procedural cost (no erroneous selection of non-fitting catheters)

f. Less radiation burden for the patient g. Less contrast needed h. Saves opening catheters that cannot be used and associated reprocessing of inappropriate catheters The system 10 and method also contributes significantly to the avoidance of certain undesirable results associated with repeat catheter insertion and removal and reinsertion in order to locate the optimal catheter configuration for the particular procedure. In particular, the reduced number of unsuccessful attempts to insert a catheter achieved by the system 10 and associated method of use in a cardiac catheterization procedure will subsequently reduce:

i. the potential for injury in the ascending aorta and the coronary orifices;

a. the potential for "liberating" plaque material from the arterial wall with subsequent embolization into brain or a periphery;

b. the potential for mechanical injury at the arterial access site; and/or c. the overall adverse event rate of the particular procedure.

For coronary interventions in particular, the system 10 and associated method provides:

a. Better anatomic lesion characterization through pre-procedural quantitative coronary analysis (% diameter stenosis, minimal lumen diameter, etc.)

b. Functional characterization of the target lesion (FFR-CT, CT perfusion etc.)

c. Better stent selection (diameter and length) based by pre-procedural quantitative coronary analysis d. Better recognition of coronary artery calcifications that might lead to extended dissections (after balloon dilatation) and/or incomplete stent expansion with strut malapposition and a subsequently elevated risk for stent thrombosis In addition, for transcatheter aortic valve replacement (TAVR) procedures, the system 10 and associated method provides the capability for:

a. Pre-selection of optimally fitting prosthesis;

b. Orientation for insertion angle;

c. Recognition of ascending aorta abnormalities (coronary orifices etc.); and d. Recognition of factors leading to para-valvular leaks (oval rather than round aortic annulus).

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A catheter selection system for determining a catheter having an optimized configuration for use in a medical procedure, the selection system comprising:

a scanning device capable of obtaining image data on a region of interest (ROI) within the anatomy of a patient and reconstructing a three-dimensional (3D) image of the ROI from the image data;

a display capable of illustrating the 3D ROI image and a 3D catheter model;

a central processing unit (CPU) operably connected to the scanning device and the display, the CPU operable to analyze the 3D ROI image in comparison with the 3D catheter model; and a database of available catheter models currently in a hospital inventory operably connected to the CPU.

2. The catheter selection system of claim 1 wherein the scanning device is selected from the group consisting of: a magnetic resonance imaging (MRI) device, an x-ray computed tomography (CT) device and a 3D angio-rotation scanning device.

3. The catheter selection system of claim 1 further comprising an operator console operably connected to the CPU.

* * * * *